United States Patent
Pohl et al.

(10) Patent No.: US 7,279,457 B2
(45) Date of Patent: Oct. 9, 2007

(54) RAPID ACTING DRUG DELIVERY COMPOSITIONS

(75) Inventors: Roderike Pohl, Sherman, CT (US); Solomon S. Steiner, Mount Kisco, NY (US)

(73) Assignee: Biodel, Inc., Danbury, CT (US)

( * ) Notice: Subject to any disclaimer, the term of this patent is extended or adjusted under 35 U.S.C. 154(b) by 316 days.

(21) Appl. No.: 11/077,604

(22) Filed: Mar. 11, 2005

(65) Prior Publication Data

US 2005/0214251 A1 Sep. 29, 2005

Related U.S. Application Data

(60) Provisional application No. 60/552,637, filed on Mar. 12, 2004, provisional application No. 60/609,194, filed on Sep. 9, 2004.

(51) Int. Cl.
*A61K 38/28* (2006.01)
*C07K 16/00* (2006.01)

(52) U.S. Cl. .............. 514/3; 514/4; 514/866; 514/951; 514/953; 514/959; 530/303; 530/304

(58) Field of Classification Search ............ 514/3, 514/4, 866, 951, 953, 959; 530/303, 304
See application file for complete search history.

(56) References Cited

U.S. PATENT DOCUMENTS

| | | | | |
|---|---|---|---|---|
| 5,514,646 | A | * | 5/1996 | Chance et al. ......... 514/3 |
| 5,547,929 | A | * | 8/1996 | Anderson et al. ........ 514/3 |
| 5,573,396 | A | | 11/1996 | Swanson |
| 5,763,396 | A | | 6/1998 | Weiner et al. |
| 5,785,989 | A | | 7/1998 | Stanley et al. |
| 5,807,315 | A | * | 9/1998 | Van Antwerp et al. ..... 604/502 |
| 5,849,322 | A | | 12/1998 | Ebert et al. |
| 5,929,027 | A | | 7/1999 | Takama et al. |
| 6,395,744 | B1 | | 5/2002 | Adams et al. |
| 6,432,383 | B1 | | 8/2002 | Modi |
| 6,676,931 | B2 | | 1/2004 | Dugger, III. |
| 6,949,258 | B2 | | 9/2005 | Zhang |
| 7,030,084 | B2 | | 4/2006 | Ekwuribe et al. |
| 2003/0064097 | A1 | | 4/2003 | Patel et al. |
| 2003/0068378 | A1 | | 4/2003 | Chen et al. |
| 2003/0194420 | A1 | | 10/2003 | Holl et al. |
| 2004/0151774 | A1 | | 8/2004 | Pauletti et al. |
| 2004/0247628 | A1 | | 12/2004 | Lintz et al. |

FOREIGN PATENT DOCUMENTS

| WO | WO 95/34294 | 12/1995 |
|---|---|---|
| WO | WO 97/49386 | 12/1997 |
| WO | WO 03/057170 | 7/2003 |
| WO | WO 03/086345 | 10/2003 |
| WO | WO 2004/056314 | 7/2004 |

OTHER PUBLICATIONS

Costello et al. Zinc Inhibition of Mitochondrial Aconitase and Its Importance in Citrate Metabolism of Protease Epithelial Cells, Nov. 14, 1997, The Journal of Biological Chemistry, vol. 272, No. 46, pp. 28875-28881.*
Brange and Langkjoer, "Insulin structure and stability", *Pharm Biotechnol.*, 5:315-50 (1993).
Dunn, "Zinc-ligand interactions modulate assembly and stability of the insulin hexamer", *Biometals.*, 18(4):295-303 (2005).
Prabhu, et al., "A study of factors controlling dissolution kinetics of zinc complexed protein suspensions in various ionic species", *Int J Pharm.*, 217(1-2):71-8 (2001).
US 5,785,981, 07/1998, Stanley et al. (withdrawn)

* cited by examiner

*Primary Examiner*—Cecilia J. Tsang
*Assistant Examiner*—Abdel A Mohamed
(74) *Attorney, Agent, or Firm*—Pabst Patent Group LLP

(57) ABSTRACT

Drug formulations for systemic drug delivery with improved stability and rapid onset of action are described herein. The formulations may be administered via buccal administration, sublingual administration, pulmonary delivery, nasal administration, subcutaneous administration, rectal administration, vaginal administration, or ocular administration. In the preferred embodiments, the formulations are administered sublingually or via subcutaneous injection. The formulations contain an active agent and one or more excipients, selected to increase the rate of dissolution. In the preferred embodiment, the drug is insulin, and the excipients include a metal chelator such as EDTA and an acid such as citric acid. Following administration, these formulations are rapidly absorbed by the oral mucosa when administered sublingually and are rapidly absorbed into the blood stream when administered by subcutaneous injection. In one embodiment, the composition is in the form of a dry powder. In another embodiment, the composition is in the form of a film, wafer, lozenge, capsule, or tablet. In a third embodiment, a dry powdered insulin is mixed with a diluent containing a pharmaceutically acceptable carrier, such as water or saline, a metal chelator such as EDTA and an acid such as citric acid. Devices for storing and mixing these formulations are also described.

13 Claims, 7 Drawing Sheets

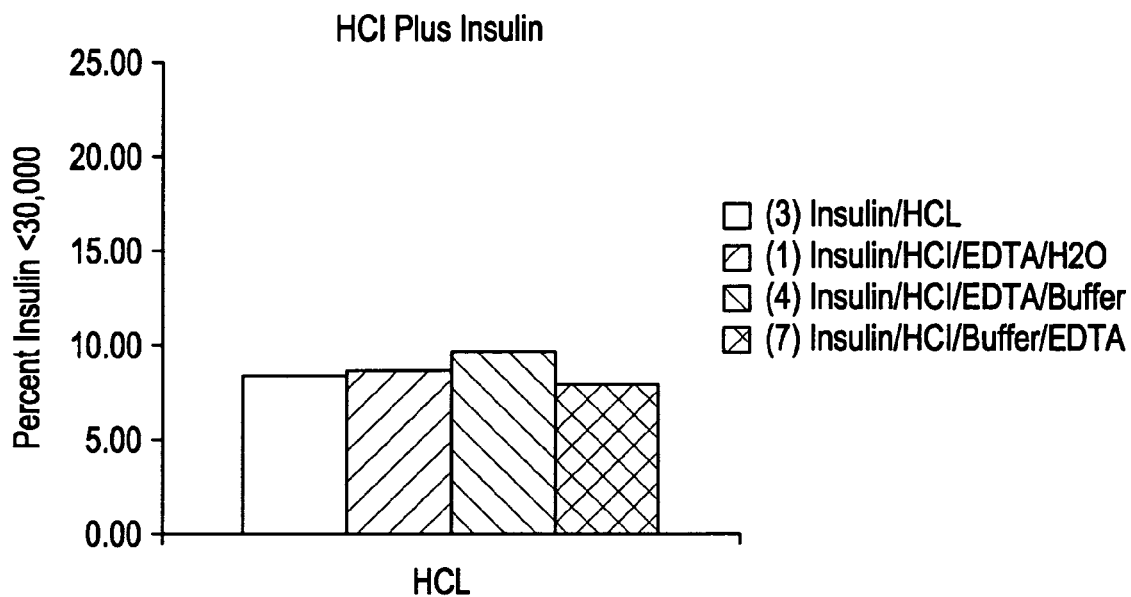
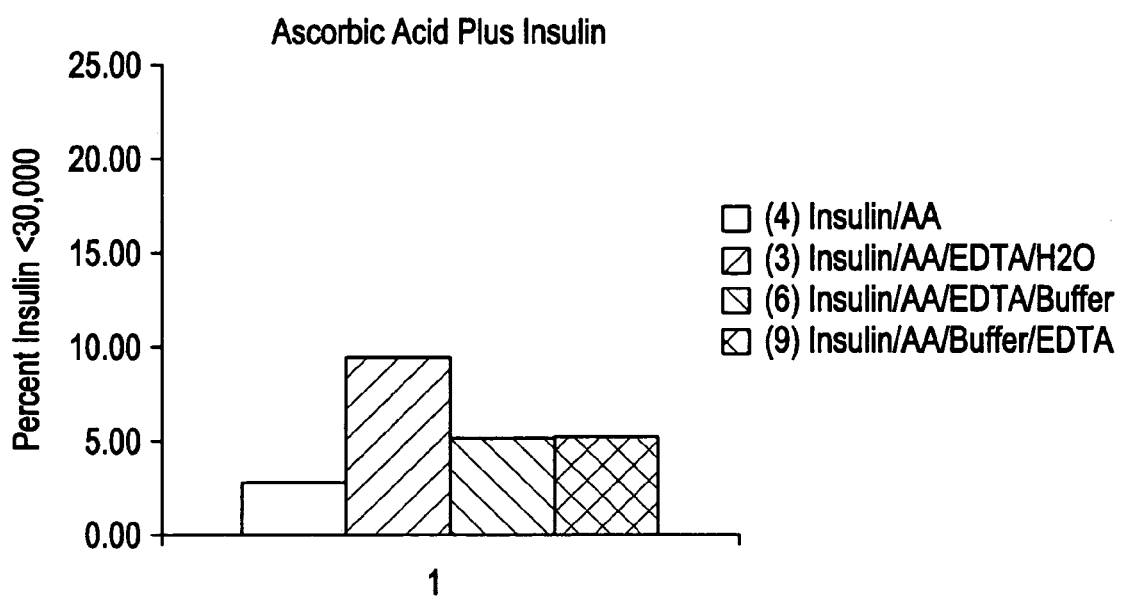

RAPID ACTING DRUG DELIVERY COMPOSITIONS

CROSS-REFERENCE TO RELATED APPLICATIONS

This application claims priority to U.S. Ser. No. 60/552,637, entitled "Sublingual Drug Delivery Compositions" to Roderike Pohl and Solomon S. Steiner filed Mar. 12, 2004, and U.S. Ser. No. 60/609,194, entitled "Sublingual Drug Delivery Compositions" to Roderike Pohl and Solomon S. Steiner filed Sep. 9, 2004.

FIELD THE INVENTION

The invention is in the general field of rapid acting drug delivery formulations.

BACKGROUND OF THE INVENTION

An effective, non-invasive oral delivery system for peptides, in general, and insulin, in particular, has not been developed to date, due to several limiting factors. First, tablets or liquids containing peptides, such as insulin, are readily digested in the harsh stomach environment, and thus require extensive protection to survive and be absorbed. Food effects and individual gastrointestinal (GI) transit times confound a dependable temporal or quantitative delivery.

The lack of effective oral delivery means is further complicated in some cases. For example, insulin is most stable in its hexameric form (six insulin monomers assembled around zinc ions). Therefore, it is preferable to store it in this form for greater shelf-life stability. However, this form is too large for rapid absorption though tissue membranes.

U.S. Pat. No. 6,676,931 to Dugger, III discloses liquid sprays that deliver an active agent to the mouth for absorption through the oral mucosa. U.S. Pat. No. 6,676,931 notes that the active agent may be insulin lispro, which is a rapidly-acting human insulin analog that contains hexameric insulin. However, such liquid sprays are not very useful for delivering hexameric insulin due to its poor absorption. Additionally, many active agents are not stable in the liquid form and cannot be stored in liquid form.

Buccal administration using sprays of insulin has been attempted with limited bioavailability since hexameric insulin is not readily absorbed and liquids are eventually swallowed. The administered dose is not rapidly absorbed, and has an absorption profile similar to subcutaneous injection. Also, due to its poor bioavailability, a large dose is required for a useful glucose lowering effect. Thus, it is not a cost effective or therapeutic alternative.

Pulmonary formulations are being developed and may provide a good alternative to injection. However, these formulations require the use of an inhaler and may lack good patient compliance if the delivery technique is complicated.

Therefore it is an object of the invention to provide oral drug delivery compositions with improved stability and rapid onset of action.

It is a further object of the invention to provide methods for storing drugs and rapidly delivering drugs.

SUMMARY OF THE INVENTION

Drug formulations for systemic drug delivery with improved stability and rapid onset of action are described herein. The formulations may be administered via buccal administration, sublingual administration, pulmonary delivery, nasal administration, subcutaneous administration, rectal administration, vaginal administration, or ocular administration. In the preferred embodiments, the formulations are administered sublingually or via subcutaneous injection. The formulations contain an active agent and one or more excipients selected to increase the rate of dissolution. In the preferred embodiment, the drug is insulin, and the excipients include a metal chelator such as EDTA and an acid such as citric acid. Following administration, these formulations are rapidly absorbed by the oral mucosa when administered sublingually and are rapidly absorbed into the blood stream when administered by subcutaneous injection. In one embodiment, the composition is in the form of a dry powder. In another embodiment, the composition is in the form of a film, wafer, lozenge, capsule, or tablet. In a third embodiment, a dry powdered insulin is mixed with a diluent containing a pharmaceutically acceptable carrier, such as water or saline, a metal chelator such as EDTA and an acid such as citric acid. Devices for storing and mixing these formulations are also described.

BRIEF DESCRIPTION OF THE DRAWINGS

FIGS. 5a-5d are graphs of the percent of low molecular weight insulin in the presence of HCl (FIG. 5a), ascorbic acid (FIG. 5b), citric acid (FIG. 5c), and acetic acid (FIG. 5d), alone or in combination with EDTA, at either pH 3.0 or pH 7.0.

DETAILED DESCRIPTION OF THE INVENTION

I. Compositions

Figure 1A:
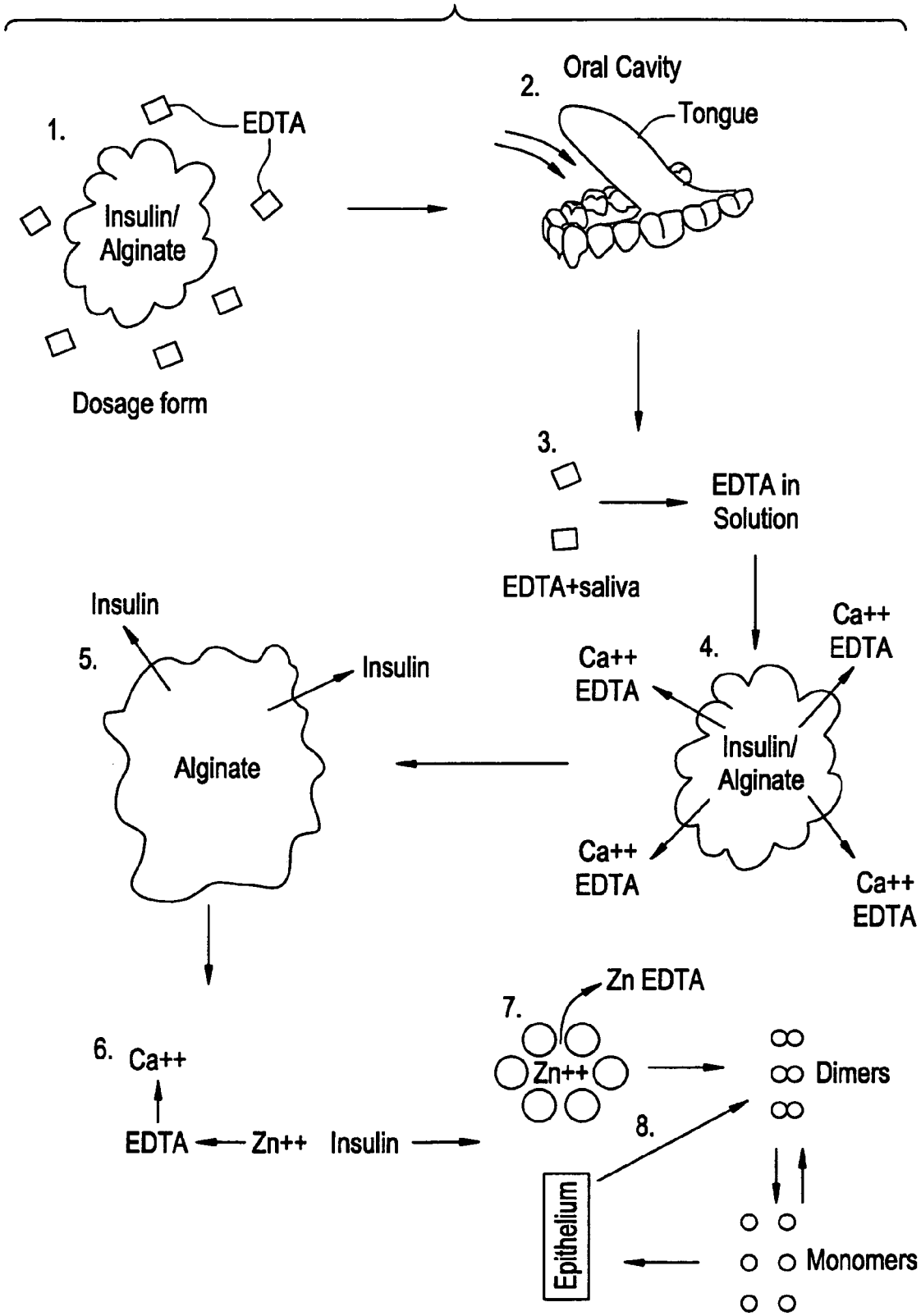
FIG. 1a is a schematic for the delivery of a dry powder insulin composition.

Formulations including an active agent, such as insulin, and one or more excipients, such as a chelator and/or solubilizing agent, that dissolve rapidly in aqueous media are described herein. In the preferred embodiment, the formulations are suitable for subcutaneous or sublingual administration. These formulations are rapidly absorbed through mucosal surfaces (parenteral, pulmonary, etc.) and through the fatty tissue when administered subcutaneously.

This is achieved through the addition of excipients, especially solubilizers such as acids and metal chelators.

Definitions

As generally used herein, a drug is considered "highly soluble" when the highest dose strength is soluble in 250 ml or less of aqueous media over the pH range of 1-7.5. The volume estimate of 250 ml is derived from typical bioequivalence (BE) study protocols that prescribe administration of a drug product to fasting human volunteers with a glass (about 8 ounces) of water. A drug is considered highly soluble when 90% or more of an administered dose, based on a mass determination or in comparison to an intravenous reference dose, is dissolved. Solubility can be measured by the shake-flask or titration method or analysis by a validated stability-indicating assay.

As generally used herein, an immediate release drug formulation is considered "rapidly dissolving" when no less than 85% of the labeled amount of the drug substance dissolves within 30 minutes, using U.S. Pharmacopeia (USP) Apparatus I at 100 rpm (or Apparatus II at 50 rpm) in a volume of 900 ml or less in each of the following media: (1) 0.1 N HCl or Simulated Gastric Fluid USP without enzymes; (2) a pH 4.5 buffer; and (3) a pH 6.8 buffer or Simulated Intestinal Fluid USP without enzymes.

Pharmaceutically Active Agents

Although described with reference to insulin, the formulations may be used with other agents, including peptides, proteins, nucleotide molecules (RNA sequences, DNA sequences), sugars, polysaccharides, and small organic molecules. Preferably, the active agent is at least slightly soluble in aqueous medium (i.e. 10,000 parts of aqueous solvent per solute), and more preferably is highly soluble in aqueous medium. Preferably the active agent is highly potent, so that only a small amount (e.g. in the microgram range) is needed to provide a therapeutic effect. Suitable peptides include but are not limited to insulin and derivatives of insulin, such as lispro; C-peptide; glucagon-like peptide 1 (GLP 1) and all active fragments thereof; human amylin and synthetic forms of amylin, such as pramlintide; parathyroid hormone (PTH) and active fragments thereof (e.g. $PTH_{1-34}$); calcitonin; human growth hormone (HGH); erythropoietin (EPO); macrophage-colony stimulating factor (M-CSF); granulocyte-macrophage-colony stimulating factor (GM-CSF); and interleukins. In the preferred embodiment the active agent is insulin. Sutiable small molecules include nitroglycerin, sumatriptan, narcotics (e.g. fenatnyl, codeine, propoxyphene, hydrocodone, and oxycodone), benzodiazepines (e.g. Alprazolam, Clobazam, Clonazepam, Diazepam Flunitrazepam, Lorazepam, Nitrazepam, Oxazepam, Temazepam, and Triazolam), phenothiazines (Chlorpromazine, Fluphenazine, Mesoridazine, Methotrimeprazine, Pericyazine, Perphenazine, Prochlorperazine, Thioproperazine, Thioridazine, and Trifluoperazine), and selective serotonin reuptake inhibitors (SSRIs) (e.g. sertraline, fluvoxamine, fluoxetine, citalopram, and paroxetine).

In the preferred embodiment, the active agent is insulin or an analog or derivative thereof. The insulin can be recombinant or purified. In the preferred embodiment, the insulin is human insulin. Recombinant human insulin is available from a number of sources.

The dosages of the active agents depend on their bioavailability and the disease or disorder to be treated. Insulin is generally included in a dosage range of 12 to 2000 IU per human dose. Thus if the insulin has a bioavailability 5-25%, the actual systemic dose delivered to an individual ranges from 3 to 100 IU. For insulin with only 2.5% bioavailability, an oral dose of 4,000 IU will deliver a 100 IU systemically available dose. For insulin with a much greater bioavailability, such as a 50% bioavailability, the delivery of a 3 IU systemically available dose requires an oral dose of 6 IU.

Formulations

The compositions contain one or more excipients. In the preferred embodiment, at least one of the excipients is selected to mask any charges on the active agent. This facilitates the transmembrane transport for the active agent and thereby increases both the onset of action and bioavailability for the active agent. The excipients are also selected to form compositions that dissolve rapidly in aqueous medium. Optional pharmaceutically acceptable excipients present in the drug-containing tablets, beads, granules or particles include, but are not limited to, diluents, binders, lubricants, disintegrants, colorants, stabilizers, and surfactants.

Solubilizing Agents

In the preferred embodiment, one or more solubilizing agents are included with the active agent to promote rapid dissolution in aqueous media. Suitable solubilizing agents include wetting agents such as polysorbates and poloxamers, non-ionic and ionic surfactants, food acids and bases (e.g. sodium bicarbonate), and alcohols, and buffer salts for pH control. Suitable acids include acetic acid, ascorbic acid, citric acid, and hydrochloric acid. For example, if the active agent is insulin, a preferred solubilizing agent is citric acid.

Chelators

In the preferred embodiment, a metal chelator is mixed with the active agent or in a coating surrounding the active agent. The chelator may be ionic or non-ionic. Suitable chelators include ethylenediaminetetraacetic acid (EDTA), citric acid, dimercaprol (BAL), penicillamine, alginic acid, chlorella, cilantro, alpha lipoic acid, dimercaptosuccinic acid (DMSA), dimercaptopropane sulfonate (DMPS), and oxalic acid. In the preferred embodiment, the chelator is EDTA. The chelator hydrogen bonds with the active agent, thereby masking the charge of the active agent and facilitating transmembrane transport of the active agent. For example, when the active agent is insulin, in addition to charge masking, it is believed that the chelator pulls the zinc away from the insulin, thereby favoring the monomeric form of the insulin over the hexameric form and facilitating absorption of the insulin by the tissues surrounding the site of administration (e.g. mucosa, or fatty tissue). Optionally, the chelator and solubilizing agent are the same compound.

Ions may be part of the active agent, added to the stabilizing agent, mixed with the chelator, and/or included in the coating. Representative ions include zinc, calcium, iron, manganese, magnesium, aluminum, cobalt, copper, or any di-valent metal or transitional metal ion. $Zn^{+2}$ has a stronger binding preference for EDTA than $Ca^{+2}$.

Diluents and Fillers

Diluents, also referred to herein as fillers, are typically necessary to increase the bulk of a solid dosage form so that a practical size is provided for compression of tablets or formation of beads and granules. Suitable fillers include, but are not limited to, dicalcium phosphate dihydrate, calcium sulfate, lactose, sucrose, mannitol, sorbitol, cellulose, microcrystalline cellulose, powdered cellulose, kaolin, sodium chloride, dry starch, hydrolyzed starches, pregelatinized starch, silicone dioxide, titanium oxide, magnesium aluminum silicate, calcium carbonate, compressible sugar, sugar spheres, powdered (confectioner's) sugar, dextrates, dextrin, dextrose, dibasic calcium phosphate dehydrate, glyceryl palmitostearate, magnesium carbonate, magnesium oxide, maltodextrin, polymethacrylates, potassium chloride, talc, and tribasic calcium phosphate.

Binders

Binders are used to impart cohesive qualities to a solid dosage formulation, and thus ensure that a tablet, bead or granule remains intact after the formation of the dosage forms. Suitable binder materials include, but are not limited to, starch, pregelatinized starch, gelatin, sugars (including sucrose, glucose, dextrose, lactose and sorbitol), dextrin, maltodextrin, zein, polyethylene glycol, waxes, natural and synthetic gums such as acacia, guar gum, tragacanth, alginate, sodium alginate, celluloses, including hydroxypropylmethylcellulose, carboxymethylcellulose sodium, hydroxypropylcellulose, hydroxyethylcellulose, ethylcellulose, methyl cellulose, and veegum, hydrogenated vegetable oil, Type I, magnesium aluminum silicate, and synthetic polymers such as acrylic acid and methacrylic acid copolymers, carbomer, methacrylic acid copolymers, methyl methacrylate copolymers, aminoalkyl methacrylate copolymers, polyacrylic acid/polymethacrylic acid, and polyvinylpyrrolidone.

Lubricants

Lubricants are used to facilitate tablet manufacture. Examples of suitable lubricants include, but are not limited to, magnesium stearate, calcium stearate, stearic acid, glyceryl behenate, glyceryl monostearate, glyceryl palmitostearate, hydrogenated castor oil, hydrogenated vegetable oil, type I, sodium benzoate, sodium lauryl sulfate, sodium stearyl fumarate, polyethylene glycol, talc, zinc stearate, and mineral oil and light mineral oil.

Disintegrants

Disintegrants are used to facilitate dosage form disintegration or "breakup" after administration, and generally include, but are not limited to, starch, sodium starch glycolate, sodium carboxymethyl starch, methylcellulose, calcium carboxymethylcellulose, sodium carboxymethylcellulose, hydroxypropyl cellulose, microcrystalline cellulose, colloidal silicon dioxide, croscarmellose sodium, pregelatinized starch, clays, cellulose, powdered cellulose, pregelatinized starch, sodium starch glycolate, sodium aginate, alginic acid, guar gum, magnesium aluminum silicate, polacrilin potassium, and cross linked polymers, such as cross-linked PVP, crospovidone (POLYPLASDONE® XL from GAF Chemical Corp).

Stabilizers

Stabilizers are used to inhibit or retard drug decomposition reactions which include, by way of example, oxidative reactions. A number of stabilizers may be used. Suitable stabilizers include polysaccharides, such as cellulose and cellulose derivatives, and simple alcohols, such as glycerol; bacteriostatic agents such as phenol, m-cresol and methylparaben; isotonic agents, such as sodium chloride, glycerol, and glucose; lecithins, such as example natural lecithins (e.g. egg yolk lecithin or soya bean lecithin) and synthetic or semisynthetic lecithins (e.g. dimyristoylphosphatidylcholine, dipalmitoylphosphatidylcholine or disterarotyl-phosphatidylcholine; phosphatidic acids; phosphatidylethanolamines; phosphatidylserines such as distearoylphosphatidylserine, dipalmitoylphosphatidylserine and diarachidoylphosphatidylserine; phosphatidylglycerols; phosphatidylinositols; cardiolipins; sphingomyelins; and synthetic detergents, such as dioctanoylphosphatidyl choline and polyethylene-polypropylene glycol). Other suitable stablizers include acacia, albumin, alginic acid, bentonite, carboxymethylcellulose calcium, carboxymethylcellulose sodium, cyclodextrins, glyceryl monostearate, hydroxypropyl cellulose, hydroxypropyl methylcellulose, magnesium aluminum silicate, propylene glycol, propylene glycol alginate, sodium alginate, white wax, xanthan gum, and yellow wax. In the preferred embodiment, the agent is insulin and the stabilizer may be a combination of one or more polysaccharides and glycerol, bacteriostatic agents, isotonic agents, lecithins, or synthetic detergents.

Surfactants

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, ® Polyethlylene-polypropylene glycol (POLOXAMER® 401), stearoyl monoisopropanolamide, and polyoxyethylene hydrogenated tallow amide. Examples of amphoteric surfactants include sodium N-dodecyl-beta-alanin-e, sodium N-lauryl-beta-iminodipropionate, myristoamphoacetate, lauryl betaine and lauryl sulfobetaine.

If desired, the tablets, wafers, films, lozenges, beads, granules, or particles may also contain minor amount of nontoxic auxiliary substances such as dyes, sweeteners, coloring and flavoring agents, pH buffering agents, or preservatives.

Polymers

Blending or copolymerization sufficient to provide a certain amount of hydrophilic character can be useful to improve wettability of the materials. For example, about 5% to about 20% of monomers may be hydrophilic monomers. Hydrophilic polymers such as hydroxylpropylcellulose (HPC), hydroxpropylmethylcellulose (HPMC), carboxymethylcellulose (CMC) are commonly used for this purpose. Also suitable are hydrophobic polymers such as polyesters and polyimides. It is known to those skilled in the art that these polymers may be blended with polyanhydrides to achieve compositions with different drug release profiles and mechanical strengths. Preferably, the polymers are bioerodable, with preferred molecular weights ranging from 1000 to 15,000 Da, and most preferably 2000 to 5000 Da.

Formulations

The active compounds (or pharmaceutically acceptable salts thereof) may be administered in the form of a pharmaceutical composition wherein the active compound(s) is in admixture or mixture with one or more pharmaceutically acceptable carriers, excipients or diluents. Suitable dosage forms include powders, films, wafers, lozenges, capsules, and tablets. The compositions may be administered in a variety of manners, including buccal administration, nasal administration, pulmonary administration, sublingual administration, and subcutaneous administration. Following administration, the dosage form dissolves quickly releasing the drug or forming small particles containing drug, optionally containing one or more excipients.

The formulation may dissolve in a time period ranging from 1 second to 3 minutes, 3 to 5 minutes, 5 to 8 minutes, or 8 to 12 minutes. The preferred dissolution time is less than 30 seconds. Preferably the drug is absorbed and transported to the plasma quickly, resulting in a rapid onset of action (preferably beginning within about 5 minutes following administration and peaking at about 15-30 minutes following administration).

In one preferred embodiment, the formulation is a sublingual solid formulation that contains an active agent, and at least one solubilizing agent, along with other standard excipients, such as poly(vinyl alcohol), glycerin, carboxymethyl cellulose (CMC), and optionally poly(ethylene glycol) and water. In the preferred embodiment the active agent is insulin and the solubilizing agents are ethylenediamintetraacetic acid (EDTA), and citric acid. The sublingual composition may be in the form of a dry powder, monolayer, bilayer, or trilayer film, a lyophilized wafer, lozenge, capsule, or a tablet.

In a second preferred embodiment, the formulation is in a form sutiable for subcutaneous injection. In this embodiment, the formulation is formed by mixing a powdered active agent with a liquid diluent that contains a pharmaceutically acceptable liquid carrier and one or more solubilizing agents. In the preferred embodiment, the active agent is insulin, and the diluent contains saline, EDTA and citric acid. Prior to administration the powder and diluent are mixed together to form an injectable composition.

Dry Powder

The composition may be in the form of a dry powder containing the pharmaceutically active agent and one or more excipient(s). Typically the dry powder composition is in a form suitable for oral, nasal or pulmonary administration. Typical routes for oral administration include buccal delivery and sublingual delivery. Preferably the composition is delivered sublingually. The active agent and excipient may be stored together or separately. The active agent and excipients may be stored together if the active agent is stable in the presence of the excipients. Alternatively, they may be stored separately, and then mixed before, during or after they are dispensed to the oral cavity. The powder rapidly dissolves upon mixing with saliva and effectively delivers the active agent to the systemic circulation via absorption through the sublingual epithelium.

The active agents and excipients may be in the form of particles having the same or different sizes. In one embodiment, the excipient particles are larger than the particles of agent. This will allow the small particles of agent to coat the larger particle so that both particles are administered simultaneously. Typically, the average particle diameter for the agent particles is less than or equal to one-tenth of the average particle diameter for the excipient particles. For sublingual delivery, the large particles generally have diameters greater than 8 µm, preferably greater than 20 µm. The average diameters for the large particles typically range from 8 µm to 500 µm, preferably from 50 µm to 150 µm. The small particles generally have a diameter ranging from 1 nm to 9 µm, preferably from 100 nm to 400 nm. For buccal and nasal administration, the particles generally have similar size ranges to those described from sublingual administration. For pulmonary administration, the large particles typically have an average diameter ranging from 1 µm to 10 µm, preferably from 2 µm to 5 µm; and the small particles typically have an average diameter ranging from 10 nm to 1 µm.

If the particles of excipient have generally the same size, the average diameters will generally be greater than 8 µm, preferably greater than 20 µm, with typical size ranges from 8 µm to 500 µm, and preferably from 50 µm to 150 µm (for sublingual, buccal and nasal administration); and from 1 µm to 10 µm, preferably from 2 µm to 5 µm (for pulmonary administration).

Optionally, the particles are oppositely charged, so that the excipient particles contain one charge and the agent particles contain the opposite charge so that the particles are administered simultaneously. The particles may be charged by blowing them into a chamber formed of plastic surfaces, which impart charge to the particles. Two oppositely charged chambers may be used. The charged particles may be formed by using an acidic solution to make one of the particles, and a basic solution to form the other particles. Alternatively, charge can be transferred through ion discharge (e.g. using a staticizer or destaticizer). If the particles of agent and excipient are oppositely charged, they may have the same average diameter or different average diameters.

In one embodiment, the components are stored separately, either in separate containers, a blister pack or capsules, which are combined at the time of administration. In one embodiment, shown in FIG. 2, the container is an ampoule 20 wherein the insulin is present in powdered form in the cap 22, separated from a solution 24 containing citric acid and EDTA. At the time of administration, the insulin is added to the solution 24 and administered. This may be accomplished by breaking a seal located at the bottom 26 of the cap 22, for example, made of a polyethylene, which is ruptured by rotating the cap 22.

Film

The composition may be in the form of a film. The film is a clear or opaque, flexible, thin material. Typical thicknesses range from 0.01 to 2 mm. The film may have any suitable shape, including round, oval, rectangle, or square. The film may be a monolayer, bilayer or trilayer film. In the preferred embodiment, the film is designed to be suitable for sublingual administration. The monolayer film contains an active agent and one or more excipients. The bilayer film contains one or more excipients, such as a solubilizing agent and/or a metal chelator, in a first layer, and an active agent in the second layer. This configuration allows the active agent to be stored separated from the excipients, and may increase the stability of the active agent, and optionally increases the shelf life of the composition compared to if the excipients and active agent were contained in a single layer. The trilayer film contains three layers of film. Each of the layers may be different, or two of the layers, such as the bottom and top layers, may have substantially the same composition. In one embodiment, the bottom and top layers surround a core layer containing the active agent. The bottom and top layers may contain one or more excipients, such as a solubilizing agent and a metal chelator. Perferably the bottom and top layers have the same composition. Alternatively, the bottom and top layers may contain different excipient(s), or different amounts of the same excipient(s). The core layer typically contains the active agent, optionally with one or more excipients.

In the preferred embodiment, the film is a bilayer film that contains EDTA and citric acid in one layer and insulin in the second layer. Each layer may contain additional excipients, such as glycerin, polyvinyl alcohol, carboxymethyl cellulose, and optionally PEG (such as PEG 400 or PEG 1600). In one embodiment, a third layer can be located between the active agent layer and the layer containing the other ingredients to further protect the active agent from degradative ingredients located in the other layer during storage. Suitable materials for the protective layer include carboxymethylcellulose sodium, carnauba wax, cellulose acetate phthalate, cetyl alcohol, confectioner's sugar, ethylcellulose, gelatin, hydroxyethyl cellulose, hydroxypropyl methylcellulose, liquid glucose, maltodextrin, methylcellulose, microcrystalline wax, polymethacrylates, polyvinyl alcohol, shellac, sucrose, talc, titanium dioxide, and zein.

By altering the composition of the excipients, the film can be designed to dissolve rapidly (less than 30 seconds) or slowly (up to 15 minutes) in order to achieve the desired absorption profile and subsequent effect. The film may dissolve in a time period ranging from 3 to 5 minutes, 5 to 8 minutes, or 8 to 12 minutes. Preferably, the film dissolves in a time period ranging from 15 seconds to 2 minutes.

Lozenge, Tablet, Capsule, or Wafer

In another embodiment, the composition is in the form of a lozenge, tablet, capsule, or wafer containing the active agent and one or more excipients, such as chelators, stabilizing agents, solubilizing agents.

Lozenge

The lozenge core is composed of a solid gel or a lyophilized wafer, containing an active agent in the core. Optionally, the core also contains a stabilizing agent, optionally with one or more additional excipients. Optionally, the upper and lower surfaces of the lozenge core are coated with a chelator, such as sodium EDTA. Alternatively, the chelator may be mixed with the active agent in the core. In the preferred embodiment, the core contains alginate (preferably calcium stabilized alginate), citric acid, EDTA, and insulin. The lozenge covers a large surface area with a thin layer, and can be made in any convenient shape. Typically it has a round or oval shape. Generally, the lozenge has a diameter and thickness that is approximately the same as the diameter and thickness of a dime. In one embodiment, the lozenge contains glycerine.

Tablet

In one embodiment, the tablet is a compressed homogenous powder of all of the ingredients. In another embodiment, inactive ingredients, such as the filler and binding agent, and one or more excipients, including the solubilizing agents, are formed into one tablet. The active agent along with filler, binding agent, and other excipients are formed into another tablet. Then the two tablets are placed together and coated to form a single tablet. Optionally, the tablet is coated with an enteric coating.

Wafer

The composition may be in the form of a wafer. The wafer is a flat, solid dosage form. Typical thicknesses range from 0.1 mm to 1.5 cm. Typical diameters range from 0.2 to 5 cm. The wafer may be in any suitable shape, including round, oval, rectangular, or square. The wafer may be a monolayer, bilayer or trilayer. In the preferred embodiment, the wafer is designed to be suitable for sublingual administration. The monolayer wafer contains an active agent and one or more excipients. The bilayer wafer contains one or more excipients, such as a solubilizing agent and/or a metal chelator, in a first layer and an active agent in the second layer. This configuration allows the active agent to be stored separated from the excipients, and may increase the stability of the active agent, and optionally increases the shelf life of the composition compared to if the excipients and active agent were contained in a single layer. The trilayer wafer contains three layers. Each of the layers may be different, or two of the layers, such as the bottom and top layers may have substantially the same composition. In one embodiment, the bottom and top layers surround a core layer containing the active agent. The bottom and top layers may contain one or more excipients, such as a solubilizing agent and a metal chelator. Preferably the bottom and top layers have the same composition. Alternatively, the bottom and top layers may contain different excipient(s), or different amounts of the same excipient(s). The core layer typically contains the active agent, optionally with one or more excipients.

Capsules

Another suitable dosage form is a capsule. The capsule contains a rapidly dissolving outer shell, which is typically composed of sugars, starches, polymers (and other suitable pharmaceutical materials). The capsule contains powders or granules of agent and excipient. The capsule is designed rapidly release powders or small rapidly dissolving granules into the oral cavity following administration.

Formulations for Subcutaneous Injection

The formulation may be an injectable formulation that is suitable for subcutaneous injection. The injectable formulation contains the active agent, a chelator, a solubilizing agent, and saline. In a preferred embodiment the injectable formulation contains insulin, EDTA, citric acid, and saline.

II. Methods of Making the Formulations

Pharmaceutical compositions may be formulated in a conventional manner using one or more physiologically acceptable carriers comprising excipients and auxiliaries which facilitate processing of the active compounds into preparations which can be used pharmaceutically. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980). Proper formulation is dependent upon the route of administration chosen.

The compounds may be complexed with other agents when they are formulated into the desired dosage form. If water-soluble, such formulated complex then may be formulated in an appropriate buffer, for example, phosphate buffered saline or other physiologically compatible solutions. Alternatively, if the resulting complex has poor solubility in aqueous solvents, then it may be formulated with a non-ionic surfactant such as Polyethylene glycol sorbitan monolaurate (TWEEN™), or polyethylene glycol.

Preferred methods for making the films, tablets, wafers, and subcutaneous injectible formulations are described below.

Films

The monolayer film is typically formed by first suspending inactive ingredients and the active agent in water. The suspension is transferred, such as by pouring or pipetting, to a sheet or mold. Then the suspension is dried by lyophilization to remove the water and form a film. Films may be made as one large sheet and cut to a desired size, based on the desired dosage. Alternatively formulations containing a single dose may be manufactured by forming the film using a mold. The bilayer and trilayer films are generally formed in the same manner as the monolayer film with the exception that each layer contains only certain ingredients (e.g. one layer contains the active agent and the other layer contains one ore more excipients).

Tablets

Tablets are made using a traditional compression machine with flat punches. Dry active ingredients are combined with an appropriate amount of an inert filler excipient such as a binding agent excipient, along with other suitable excipients. After mixing thoroughly, a predetermined amount of the mixture is placed into a tablet press and a tablet is formed. The depth of the tablet is determined by the quantity of ingredients. Compression should be sufficient to hold the ingredients together during dose administration, while allowing water penetration into the tablet for easy dissolution in the mouth.

Wafers

The wafer may be formed by compressing a powder, lyophilizing a cake, or evaporating a suspension, emulsion or gel (e.g. a hydrogel). A compression machine may also be used to make wafers using a larger, flatter punch. Alternatively, the mixed dry materials could be flattened or compressed between rollers to form the powder into a sheet that may be cut to an appropriate size that can be inserted in the mouth, preferably under the tongue. Dosing of the wafers can be determined by standard methods, such as altering the concentration of the active agent in the powder and keeping the wafer size uniform. Alternatively, the concentration of the powder can be maintained, and the surface area of the wafer can be increased to achieve higher doses, or decreased to lower the dosage. In one embodiment, the wafer is formed by suspending the active agent, solubilizing agents, binding agent or other excipients in a solvent such as water. A predetermined amount of the suspension is placed in wells in a plastic mold and lyophilized in the wells to remove the water and form a wafer. Alternatively, a bilayer wafer may be formed with the one or more excipients (e.g. solubilizing agent and/or binding agent) in one layer and the active agent along with the binding agent or other inert components in the second layer.

Wafers can also be made by combining the dry powders into aqueous solution, pipetting the appropriate amount of solution into molds, flash freezing and lyophilizing the material. This forms a very light wafer that dissolves very rapidly and requires little fill and binding material.

Formulations for Subcutaneous Injection

In the preferred embodiment, the subcutaneous injectable formulation is produced by mixing saline, citric acid and EDTA to form a solution and sterilizing the solution (referred to as the "diluent"). The insulin is separately added to sterile water to form a solution, filtered, and a designated amount is placed into each of a number of separate sterile injection bottles. The insulin solution is lyophilized to form a powder and should be stored separately from the diluent to retain its stability. Prior to administration, the diluent is added to the insulin injection bottle. After the predetermined amount of insulin is subcutaneously injected into the patient, the remaining insulin solution may be stored, preferably by refrigeration. The insulin solution should remain stable for at least one week.

III. Methods of Using Formulations

The formulations may be administered in a variety of manners, including buccal administration, nasal administration, pulmonary administration, sublingual administration, subcutaneous administration, rectal administration, vaginal administration, or ocular administration. Following administration, the dosage form dissolves quickly releasing the drug or forming small particles containing drug, optionally containing one or more excipients. The formulation is designed to be rapidly absorbed and transported to the plasma for systemic delivery.

Formulations containing insulin as the active agent may be administered to a type 1 or type 2 diabetic patient before or during a meal. The formulation is typically administered sublingually, or by subcutaneous injection. The formulation may also be administered by buccal, nasal or pulmonary administration. Due to the rapid absorption, the compositions can shut off the conversion of glycogen to glucose in the liver, thereby preventing hyperglycemia, the main cause of complications from diabetes and the first symptom of type 2 diabetes. As seen in Example 2, the sublingual insulin formulations deliver insulin to the blood stream of the patient quickly, resulting in a rapid onset of action (beginning at about 5 minutes following administration and peaking at about 15-30 minutes following administration). In contrast, currently available, standard, subcutaneous injections of human insulin must be administered about one hour prior to eating to provide a less than desired effect, because the insulin is absorbed too slowly to shut off the production of glucose in the liver. Additionally, if given early enough in the progression of the disease, the sublingual or subcutaneous insulin compositions may be able to slow or stop the progression of type 2 diabetes.

FIG. 1A is a schematic for administering the preferred dry powder composition, i.e. insulin, alginate, citric acid, and EDTA powder. As shown in FIG. 1A, the powder is composed of a solid, dry powder of citric acid, insulin, and EDTA powder. A device is used to dispense a single dose of dry powder under the tongue, so that the dose is evenly dispersed throughout the sublingual region of the oral cavity. The disodium EDTA rapidly dissolves in the saliva. The citric acid solubiizes the insulin, allowing it to be in solution in close proximity with the EDTA. The EDTA then chelates the zinc in the insulin, thereby releasing its calcium ions and pulling the zinc away from the insulin. This causes the insulin to take on its dimeric and monomeric form and prevents reassembly into hexamers. The monomeric form has a molecular weight that is less than one-sixth the molecular weight of the hexameric form, thereby markedly increasing both the speed and quantity of insulin absorption. The dimers and monomers are in equilibrium. Thus, as insulin monomers are absorbed through the epithelial membrane, additional dimers dissemble to form more monomers.

A similar process occurs if a bulking agent is included in the drug powder. For example, if alginate is used as a bulking agent for the insulin, the calcium embedded in the alginate is chelated by the EDTA, removing it from the gel matrix. This de-stabilizes the matrix, which releases the insulin into the local saliva, where insulin is now in close proximity to the EDTA. The EDTA identifies the zinc-insulin in close proximity, and exchanges its calcium for the zinc, for which it has a higher affinity. This releases the hexameric insulin into its dimeric form, of which a portion splits into monomers. Since these two forms exist in a concentration-driven equilibrium, as the monomers are absorbed, more monomers are created.

These small polypeptides of ~5,800 Da are now ready for epithelial absorption. Since the epithelium is relatively thin in the sublingual region, and blood vessels are readily available, the systemic absorption is fast and efficient. To the extent that the EDTA and/or citric acid hydrogen bond with the insulin, it masks the charge on the insulin, facilitating its transmembrane transport and thereby increases both the onset of action and bioavailability for insulin. Since the epithelium is relatively thin in the sublingual region, and blood vessels are readily available, the systemic absorption is fast and efficient, taking from 1 second to 15 minutes following administration. The powder may dissolve in a time period ranging from 1 second to 3 minutes, 3 to 5 minutes, 5 to 8 minutes, or 8 to 12 minutes. The preferred dissolution time is less than 5 minutes.

Figure 1B:
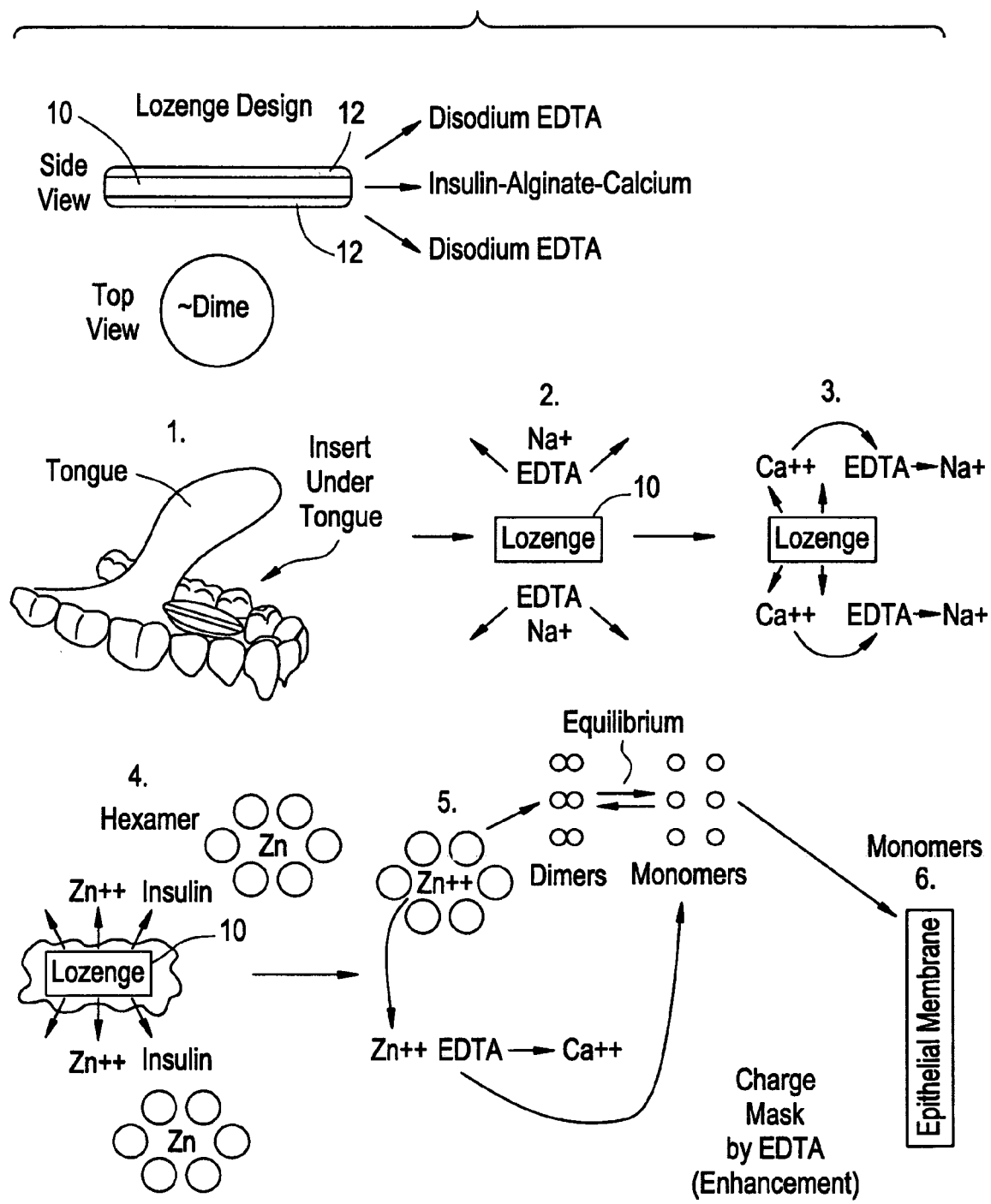
FIG. 1b is schematic for the delivery of a lozenge composition.

As described in FIG. 1B, before a meal, a lozenge is inserted under the tongue, and tongue is relaxed on top of the lozenge 10. The lozenge could be replaced with a film, wafer, tablet, or capsule. The sodium EDTA is dissolved from the surfaces 12 and into the local saliva. The surface 12 of the lozenge is wetted by the removal of the EDTA layer, providing the embedded calcium in the gel 10 with access to the surface 12. EDTA is a calcium chelator, and removes the calcium from the gel matrix, removing its supporting structure. With the calcium removed, the alginate liquefies, and releases the hexameric zinc insulin into the saliva. The EDTA is attracted to the zinc in close proximity, and removes the zinc from the insulin (for which it has a higher affinity), releasing the hexameric insulin into its dimeric form, of which a portion splits into monomers. Since the monomers and dimers exist in a concentration-driven equilibrium, as the monomers are absorbed, more monomers are created.

IV. Kits

The active agent can be stored in one container and the excipients can be stored in a second container. Immediately prior to administration the contents of both containers are mixed.

Figure 2:
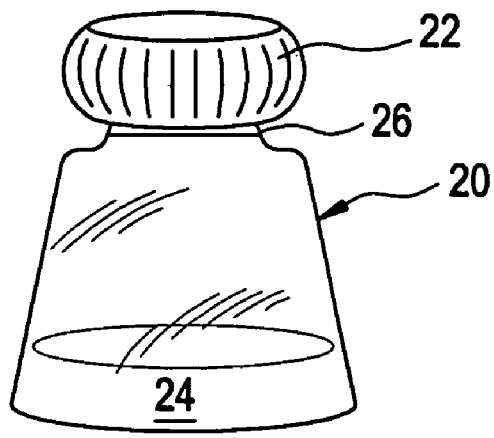
FIG. 2 is a perspective view of a vial containing powdered insulin in the cap, separated by a seal which can be broken by rotation of the cap, to allow the insulin to mix with the citric acid-EDTA solution in the vial.

As illustrated in FIG. 2, the kit may contain a vial containing powdered insulin in the cap (22), separated by a seal (26) which can be broken by rotation of the cap, to allow the insulin to mix with the excipient, e.g. citric acid-EDTA, solution in the vial (24).

The methods and compositions described above will be further understood with reference to the following non-limiting examples.

EXAMPLES

Example 1

Effect of Insulin Solutions Containing Different Concentrations of EDTA on Conversion of Insulin from a Hexameric Form to Monomer/Dimers Materials Human recombinant Insulin (Akzo-Nobel), Citric acid and disodium EDTA were used in this experiment in distilled water. NANOSEP® microtubes with 30,000 MW cutoff (Pall Scientific) were used to separate the hexamers (36,000 MW) from the dimers/monomers (6-12,000 MW) in the insulin solutions. Analysis was performed by HPLC using a waters 2695 separations module fitted with a symmetry 300.™. $C_4$ 5 um column (Waters Corp. Milford. Mass. #186000285) and a photodiode array detector (at 220 nm absorbance). A gradient method (25-32% ACN in water, 0.05% TFA) was used to separate the insulin from the other ingredients.

Methods

Human recombinant Insulin was dissolved in 2 mg/mL Citric acid to form a 1 mg/ml solution and 1.5 mL of this solution was subsequently pipetted into test tubes. EDTA was added to each tube in order to achieve a concentration of 0, 1, 2, 3, or 4 mg EDTA/mL. 0.5 mL of the combined ingredients were added to the top of the NANOSEP® microtubes and tubes were spun at 10,000 rpm for 10 minutes in a microcentrifuge (Fisher Scientific). Insulin was assayed before and after the spin, and the percent recovered in the filtrate was determined by dividing the amount of the insulin that filtered through the filter by the initial quantity placed on top.

Setup

TABLE 1

Four experimental conditions and control

| Formulation No. | Insulin (mg/ml) | EDTA (mg/mL) | Citric acid (mg/mL) |
|---|---|---|---|
| 0 | 1 | 0 | 2 |
| 1 | 1 | 1 | 2 |
| 2 | 1 | 2 | 2 |
| 3 | 1 | 3 | 2 |
| 4 | 1 | 4 | 2 |

Results

Figure 3:
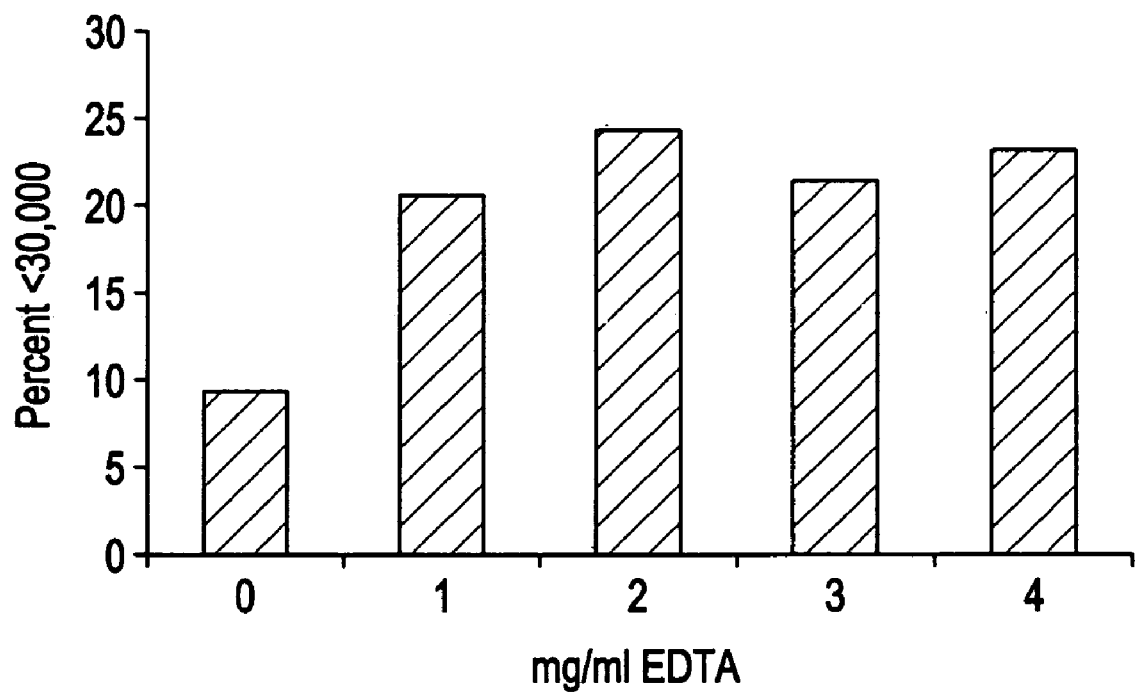
FIG. 3 is a bar graph showing the percentage of total insulin that was transferred through a 30,000 molecular weigh cut-off membrane (i.e. a filter) in the presence of varying quantities of EDTA.
Figure 4:
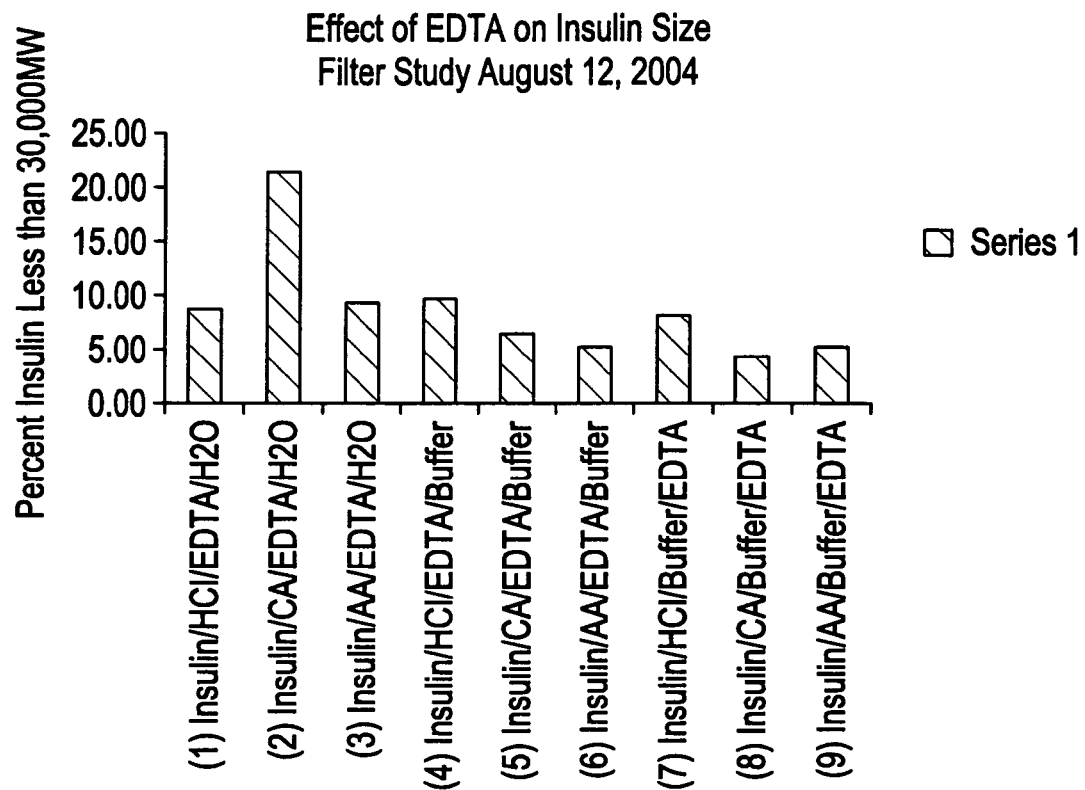
FIG. 4 is a graph of the effect of EDTA alone or in combination with citric acid, hydrochloric acid, acetic acid, and ascorbic acid, on the percent of low molecular weight (i.e., monomeric) insulin.

As shown in FIG. 3, increasing amounts of EDTA resulted in greater concentrations monomers/dimers relative to hexamer in the insulin solution. About 8% of the total insulin was filtered through the filter when no EDTA was present (control "0"). The quantity of monomer/dimers recovered in the filtrate increased to over 20% after the addition of EDTA, with a maximal effect at 2 mg/mL. Further addition of EDTA did not enhance the effect. Thus, the addition of EDTA to an insulin solution (in the presence of citric acid) increases the concentration of monomers/dimers.

Example 2

Effect of Administration of Sublingual Dry Powder Insulin Formulation on a Patient's Insulin and Glucose Levels The insulin and blood glucose levels following a single sublingual administration of a dry powder insulin formulation were measured in one male, 35-year old, Type 1 diabetic patient. The dose administered to the patient contained 6 mg insulin, 4 mg citric acid and 4 mg EDTA. The insulin in the formulation was approximately 28 IU/mg.

The patient fasted overnight and arrived at the clinic in the early morning. An IV line with a saline drip was attached to the patient. The patient was instructed to open his mouth and touch his upper palette with his tongue and the dry powder formulation was sprinkled under his tongue. He was then instructed to lower his tongue, close his mouth and not swallow for one minute.

Blood glucose was measured at five minutes prior to the application of the sublingual insulin formulation. Following administration of the insulin formulation, blood glucose was monitored in real time by the use of glucose strips and samples of blood were taken according to the times listed in Tables 2 and 3 for a laboratory determination of blood glucose concentration by the glucose oxidase method and of blood insulin concentration by a LINKO enzyme linked immunosorbent assay (ELISA).

Results and Discussion

Data obtained using the glucose strip method and glucose oxidase method are listed in Table 2.

TABLE 2

Glucose Concentrations over Time

| Time (minutes) | Strip Method Glucose concentration (mg/DL) | Oxidase Method Glucose concentration (mg/DL) |
|---|---|---|
| −5 | N/A | 99.5 |
| 3 | 84 | 96.3 |

TABLE 2-continued

Glucose Concentrations over Time

| Time (minutes) | Strip Method Glucose concentration (mg/DL) | Oxidase Method Glucose concentration (mg/DL) |
|---|---|---|
| 7 | 83 | 87.0 |
| 10 | 75 | 90.1 |
| 15 | 70 | 83.2 |
| 20 | 73 | 78.3 |
| 30 | 63 | 75.5 |
| 45 | 59 | 68.0 |
| 60 | 46 | 61.8 |
| 61 | 42 | 60.2 |
| 62 | 42 | 57.7 |
| 80 | 33 | 53.7 |
| (glucose ingestion) | | |
| 90 | 136 | 143 |
| 120 | 97 | 122.0 |
| 145 | N/A | 122.0 |
| 180 | N/A | 80.5 |

By the real-time glucose strip method, the blood glucose concentration dropped rapidly and precipitously, starting within 10-15 minutes after administration. By one hour post administration, blood glucose appeared to be dangerously low (46 mg/DL by the strip method). The initial protocol was modified at this time, and the blood glucose readings were taken more frequently. At 80 minutes post administration, the patient's blood glucose was 33 mg/DL by the strip method, and a liquid formulation of glucose was orally administered to the patient. This intervening administration of glucose was effective at raising the patient's blood glucose levels to the normal range (95-140 mg/DL) by the strip method. In contrast to this oral dosage, a subcutaneous injection of human insulin typically begins to lower blood glucose about 30 minutes after administration and produces a peak effect between 90 minutes and 3 hours after administration.

As seen based on the data in Table 2, the data obtained using the more accurate test for blood glucose, the oxidase method, mirrored the real time strip method, but was higher by about 12-20 mg/DL on an absolute basis.

Table 3 lists the blood insulin concentrations over time obtained by the LINKO ELISA test.

TABLE 3

Insulin concentrations over time

| Time (minutes) | Insulin concentration (µU/mL) |
|---|---|
| −5 | 16.9 |
| 3 | 13.9 |
| 7 | 22.7 |
| 10 | 21 |
| 15 | 22.95 |
| 20 | 23.4 |
| 30 | 19.7 |
| 45 | 21.2 |
| 60 | 21.9 |
| 80 | 21.1 |
| (glucose ingestion) | |
| 120 | 18.9 |
| 180 | 13.9 |

As seen in based on the data listed in Table 3, the blood insulin concentration rose very rapidly, beginning at 7 minutes after administration and reached a peak effect between 15 and 20 minutes after administration. In contrast, a subcutaneous injection of human insulin achieves maximum blood concentration about two hours after administration. Thus the dry powder sublingual formulation is about 6 to 8 times faster than a subcutaneous injection of human insulin.

Example 3

Determination of Effect of EDTA and Various Acids on Insulin Particle Size

A study was conducted to determine the effect of EDTA, a chelator, in combination with various acids: acetic acid, hydrochloric acid, ascorbic acid and citric acid, on insulin particle size. Controls included insulin with EDTA and no acid, and insulin with acid and no EDTA.

Using the same techniques described in example 1, insulin (1 mg/ml) was dissolved in a food acid, EDTA added, and the mixture on top of a 30,000 mw cutoff filer in a microtube, and then spun for 10 minutes at 10,000 rpm. Each mixture was tested at pH 3 (without buffer) and pH 7.0 (with phosphate buffer). The results were calculated as a percent of insulin recovered in the filtrate, compared to the starting quantity (percent).

The results are depicted graphically in FIGS. 4 and 5a-d. The results show that the combination of EDTA and citric acid produces a significantly greater amount of lower weight (i.e., monomeric rather than hexameric) insulin.

Example 4

Subcutaneous Administration of EDTA Insulin to Pigs

The EDTA-citric acid insulin formulation was administered by subcutaneous injection to pigs to compare the effect of EDTA and citric acid on insulin administered by subcutaneous administration with normal (hexameric) human insulin. The insulin was administered in a dosage of 25 U/ml, 2 mg EDTA/ml, 2 mg citric acid/ml. An insulin dose of 0.125 U/kg was administered. The effect on blood glucose was compared to the effect of 100 units regular human insulin, dose 0.125 U/kg.

Figure 6:
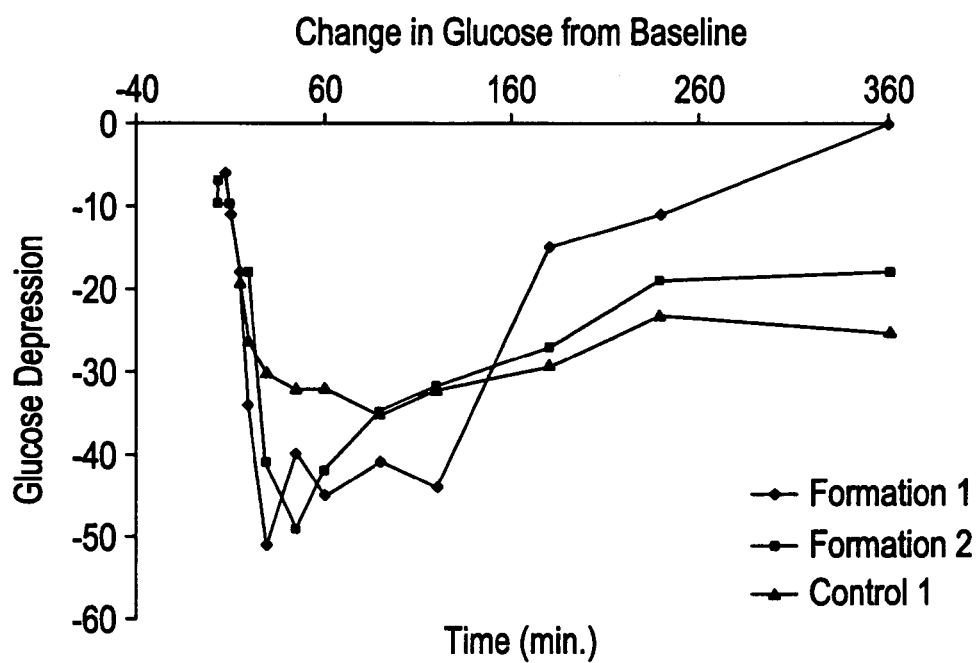
FIG. 6 is a graph of decrease in blood glucose following subcutaneous administration of insulin in combination with citric acid and EDTA.
Figure 5C:
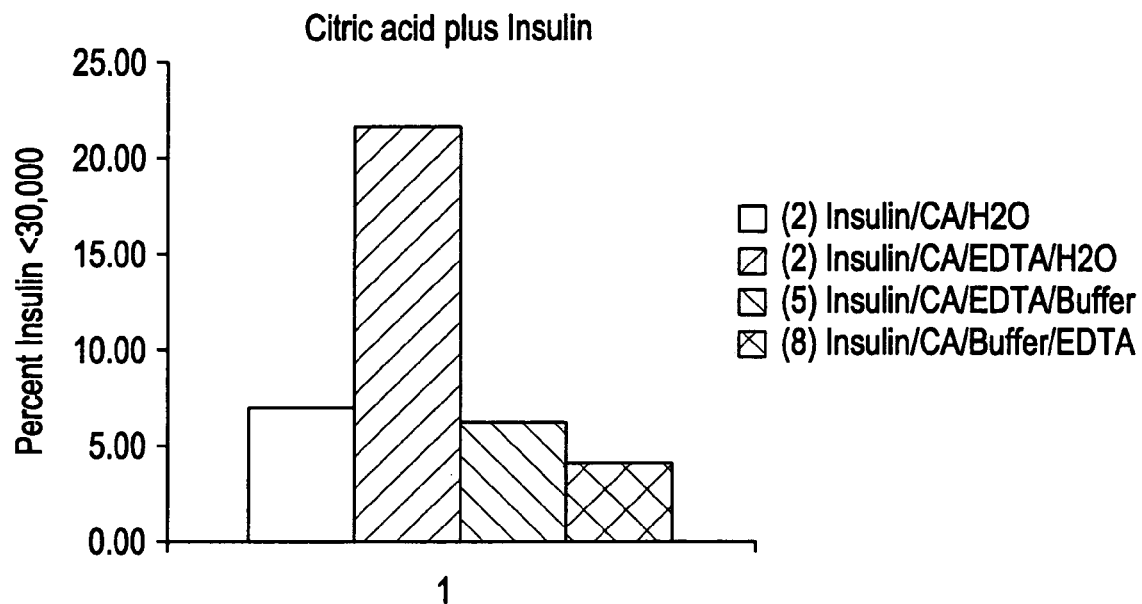
Figure 5D:
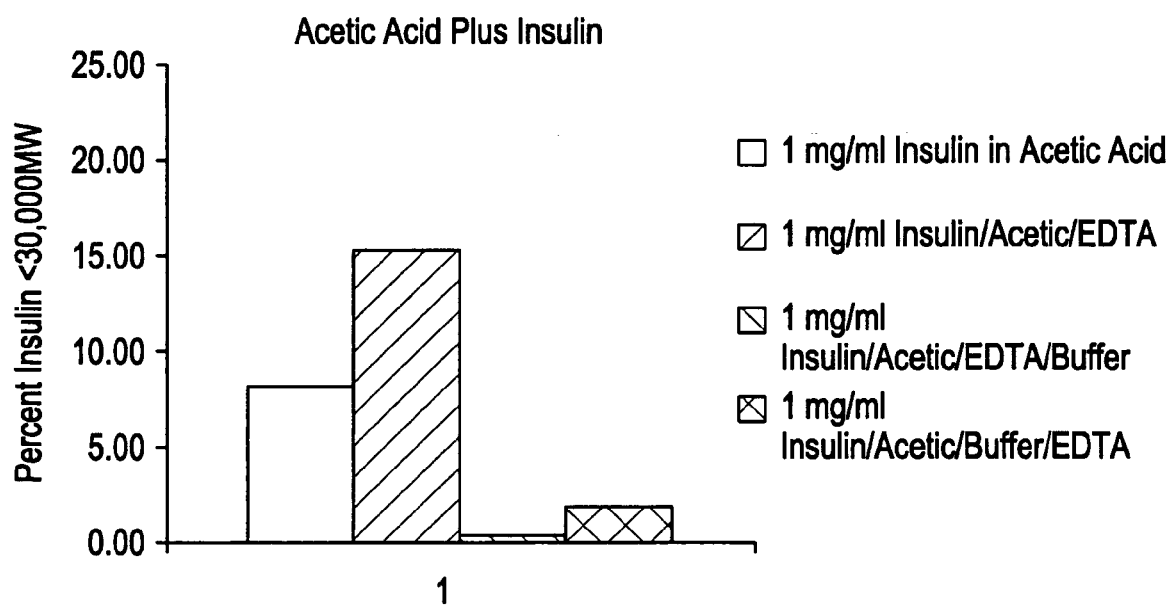

Normal human insulin normally produces its lowest glucose level at about 120 minutes after administration, with levels returning to baseline over a period of six hours. In contrast, as shown by the results in FIG. 6, the EDTA-citric acid insulin formulation produces a more rapid and significantly greater decrease in blood glucose.

Example 5

Determination of Effect of EDTA on Insulin Absorption Through a Membrane Overlayed with an Epithelial Cell Monolayer A study was conducted to demonstrate the effect of EDTA on absorption through a membrane overlayed with an epithelial cell monolayer.

Two saline solutions were mixed containing 1 mg/ml insulin, 2 mg/ml EDTA and 2 mg/ml citric acid ("solution 1") or 1 mg/ml insulin and 2 mg/ml citric acid ("solution 2"). The control solution contained only EDTA and citric acid. Immortalized epithelial cell line cultures were seeded on transwell membranes. When the cells were grown to confluence, at time zero, the fluid in the top chambers of the transwell plates was replaced with 0.5 ml of insulin solution (i.e. solution 1 or solution 2). Two plates with solution 1, two plates with solution 2 and one plate with the control solution (no cells) were tested simultaneously. The lower chamber of each plate contained 1.5 mL of saline solution. At each time point, 100 µL of fluid from the lower chamber was removed and analyzed with Enzyme-Linked Immunosorbent Assay (ELISA). 100 µL of saline was added to the lower chamber to maintain a constant volume of 1.5 mL throughout the study.

The amount of insulin removed from the lower chamber at each time point was added to the amount removed in the previous time point(s) to determine the cumulative amount of insulin recovered in the lower chamber. This data is presented in FIG. 7.

Cells were stained to check for viability before and after the experiment. There was no statistical difference in the cell viability for each of the plates.

Figure 7:
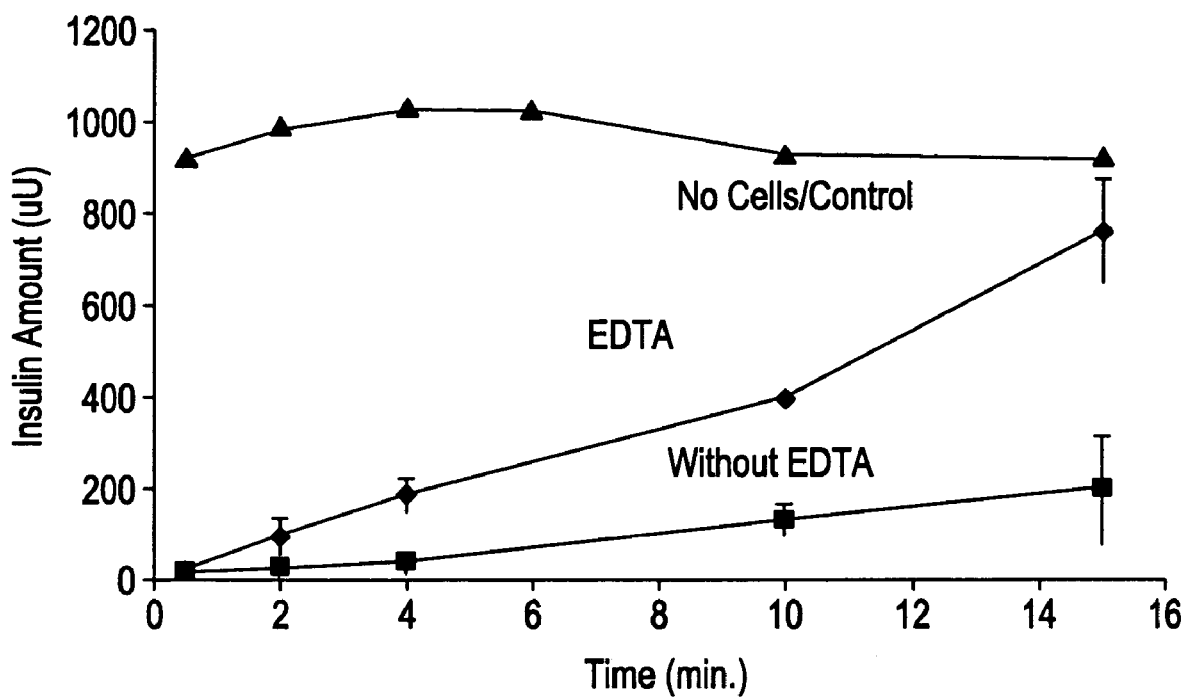
FIG. 7 is a graph of the mean insulin accumulation (μU) over time (minutes) in the lower chamber of a transwell membrane plate seeded with epithelial cells, comparing the effect of an insulin formulation containing EDTA (♦) with one without EDTA (■), with a control, no cells (▲).

The mean insulin accumulated in the lower chamber (receiver chamber) over time is shown in FIG. 7. As shown in FIG. 7, solution 1, which contained EDTA, moved through the monolayer of epithelial cells and through the membrane more effectively than solution 2, which did not contain EDTA.

Those skilled in the art will recognize, or be able to ascertain using no more than routine experimentation, many equivalents to the specific embodiments of the invention described herein. Such equivalents are intended to be encompassed by the following claims.

We claim:

1. A composition comprising a therapeutically effective dose of non-hexameric insulin, ethylenediaminetetraacetic acid (EDTA) and an acid selected from the group consisting of acetic acid, ascorbic acid, and citric acid which enhances solubility and absorption of the non-hexameric insulin in a form suitable for sublingual or subcutaneous administration.

2. The composition of claim 1, wherein the acid is present in an effective amount to mask charges on the non-hexameric insulin.

3. The composition of claim 1 wherein the acid is citric acid.

4. The composition of claim 1 in a form selected from the group consisting of dry powders, tablets, wafers, films, lozenges, and capsules.

5. The composition of claim 4, wherein the composition is in the form of a trilayer film or wafer suitable for sublingual delivery.

6. The composition of claim 1 in a form suitable for sublingual delivery.

7. The composition of claim 1, further comprising saline.

8. The composition of claim 1, in a form suitable for subcutaneous administration, wherein the agent is non-hexameric insulin, wherein the chelator is ethylenediaminetetraacetic acid (EDTA), and wherein the acid is citric acid.

9. The composition of claim 8, wherein the ratio of monomeric insulin:EDTA:citric acid is 1:2:2 (mg/ml).

10. A method of delivering insulin to a patient in need thereof comprising administering sublingually or via subcutaneous injection a composition comprising an effective amount of non-hexameric insulin, ethylenediaminetetraacetic acid (EDTA) and an acid selected from the group consisting of acetic acid, ascorbic acid, and citric acid which enhances solubility and absorption of the non-hexameric insulin.

11. The method of claim 10, wherein the acid is present in an effective amount to mask charges on the insulin.

12. The method of claim 10, wherein the acid is citric acid.

13. The method of claim 10, wherein the composition is in a form selected from the group consisting of dry powders, tablets, wafers, films, lozenges, and capsules.

* * * * *